United States Patent
Davis et al.

[11] Patent Number: 6,054,038
[45] Date of Patent: Apr. 25, 2000

[54] PORTABLE, HAND-HELD, IN-SITU ELECTROCHEMICAL SENSOR FOR EVALUATING CORROSION AND ADHESION ON COATED OR UNCOATED METAL STRUCTURES

[75] Inventors: Guy D. Davis, Baltimore; Chester M. Dacres, Columbia, both of Md.

[73] Assignee: Dacco Sci, Inc., Columbia, Md.

[21] Appl. No.: 09/093,001

[22] Filed: Jun. 8, 1998

[51] Int. Cl.[7] .............................. G01F 1/64; G01N 17/04
[52] U.S. Cl. .................. 205/776.5; 205/777; 205/791.5; 204/404; 73/86; 324/71.2; 324/693; 324/700
[58] Field of Search .............................. 205/775.5, 776.5, 205/777, 791, 791.5; 204/404, 434; 324/71.2, 693, 700; 73/86

[56] References Cited

U.S. PATENT DOCUMENTS

| | | | |
|---|---|---|---|
| 4,806,849 | 2/1989 | Kihira et al. | 204/404 |
| 4,962,360 | 10/1990 | Homma et al. | 324/700 |
| 5,221,893 | 6/1993 | Kondou et al. | 324/71.2 |
| 5,426,373 | 6/1995 | Diamond et al. | 324/663 |
| 5,746,905 | 5/1998 | Murray | 205/791 |
| 5,859,537 | 1/1999 | Davis et al. | 204/404 |
| 5,896,034 | 4/1999 | Marshall | 324/700 |

*Primary Examiner*—Robert J. Warden, Sr.
*Assistant Examiner*—Kaj K. Olsen

[57] ABSTRACT

A hand-held and flexible corrosion sensor is described that uses electrochemical impedance spectroscopy (EIS, also known as AC impedance) to detect coating degradation and corrosion of coated and uncoated metals. The hand-held and flexible corrosion sensor is pressed against the surface of the structure of specimen to be inspected, and may be either straight in structural configuration in the form of a pen or bent in a curved or angled manner to achieve better access to the structure. An EIS spectrum can than be obtained in the field or under arbitrary conditions and the degree of coating or material degradation can be determined from the resultant spectrum. There are no restrictions on the configuration of the structure being inspected. The area of detection is controlled by moderating the extent and degree of wetness of the surface. A dry surface will provide a localized measurement; a wet surface will allow inspection of the wetted area.

1 Claim, 5 Drawing Sheets

PORTABLE, HAND-HELD, IN-SITU ELECTROCHEMICAL SENSOR FOR EVALUATING CORROSION AND ADHESION ON COATED OR UNCOATED METAL STRUCTURES

BACKGROUND OF THE INVENTION

1. Field of the Invention

The present invention relates to a portable, hand-held and nondestructive corrosion sensing device for detecting the early stages of metal and coating degradation and electrochemical corrosion. More specifically, the present invention relates to a portable corrosion sensor which is utilized under field (actual, environmental or in situ) conditions in detecting coating degradation and electrochemical corrosion of both small and large coated (painted) and uncoated metal structures, thereby permitting detection of coating and metal degradation and electrochemical corrosion well before serious deterioration of the material or structure has occurred.

2. Prior Art

A major goal in the electrochemical field has long been to create a sensor which could be utilized in field or service conditions to detect corrosion and adhesion on metal structures of any size before significant degradation has occurred. Evaluation of materials and coatings and the determination or prediction of corrosion performance of both painted and uncoated metal structures or specimens under ambient field or service conditions has traditionally involved visual comparisons which are subjective and require blistering, rusting, or other advanced stages of degradation. The use of laboratory techniques, such as electrochemical impedance spectroscopy (EIS, also known as AC impedance), which has been used to understand and predict corrosion performance during immersion exposures in different electrolytes was limited to small structures or witness specimens that could be immersed, small sections of material cut from large structures, or attachment to the structure of a clamp-on liquid cell in which a liquid or semi-liquid electrolyte and remote counter and reference electrodes were contained.

Inspection of a large structure using conventional EIS methodologies required complete immersion or use of a clamp-on cell. Such cells would be filled with a liquid or semi-liquid electrolyte (e.g., Kihira et al., U.S. Pat. No. 4,806,849; and Kazami et al., U.S. Pat. No. 4,861,453) or a spongy medium impregnated with a liquid electrolyte (e.g., Kondou et al., U.S. Pat. No. 5,221,893) with remote electrodes immersed in the electrolyte or in intimate contact with the electrolyte-impregnated sponge. These cells required an accessible, flat, smooth, and horizontal area. The set-up was considered to be time consuming and had to be performed for each measurement. Corrosion was detected only directly under the cell and use of the cell actually caused artifactual damage to the coating in many instances because of exposure to the electrolyte during measurement.

Davis et al., U.S. Pat. No. 5,859,537, recently taught a painted electrode sensor which eliminates many of the problems discussed above. The actual structure is being inspected without exposure to an extrinsic electrolyte. Measurements are possible under most natural or accelerated conditions and material and coating degradation are detectable from the very early stages. However, the Davis et al., sensor requires an electrode to be permanently painted onto the structure and is time-consuming, because of all of the fabrication steps which must be completed. It is not suitable for structures in which appearance or aerodynamics preclude an attached sensor. The sensor can induce artifactual damage in a small class of materials, primarily porous coatings.

Presently, there is no portable, hand-held corrosion sensing device for early detection of electrochemical corrosion, metal and coating degradation which can evaluate degradation on structures or material of any size, under in situ or actual conditions, as well as under aggressive corrosive conditions, and which requires no permanent attachment.

SUMMARY OF THE INVENTION

The principal objective of the present invention is to provide a portable, hand-held and nondestructive corrosion sensing device which is utilized under field (actual, environmental or in situ) conditions in detecting coating degradation and electrochemical corrosion of both small and large coated (painted) and uncoated metal structures, thereby permitting detection of coating and metal degradation and electrochemical corrosion well before serious deterioration of the material or structure has occurred. The present invention allows for broad applicability, flexibility in utilizing the sensor in various environments without structural compromise and/or the ability to inspect and evaluate corrosion of the actual structure, regardless of the size of the structure.

The foregoing objectives can be accomplished utilizing the present invention as a portable, hand-held and nondestructive corrosion sensing device providing an in situ sensor for producing an output correlative to an identifiable impedance spectrum (i.e., the impedance magnitude and phase as a function of the frequency of the applied voltage, created utilizing AC Impedance or Electrochemical Impedance Spectroscopy (EIS). The preferred embodiment of the invention is a portable, hand-held and nondestructive apparatus, comprising a pen-like device which consists of a metal tip which serves both as a counter and reference electrode. The metal structure being tested, which either may be coated or uncoated, serves as the working electrode. This two electrode sensing device measures differences in impedance spectra which are responsive to atmospheric, water uptake, incubation, and corrosion; utilizing, the metal tip as the counter and reference electrode, applying a small electrical voltage between the metallic substrate of the structure, which serves as the working electrode, and the counter/reference electrode and measuring the resulting current based upon the applied voltage between the electrodes. The portable, hand-held in situ corrosion sensor contemplated in the present invention is pressed against the top coat during inspection. The present invention readily detects the early stages of interfacial degradation well before any visual indication of corrosion appears, as well as the ability to detect, quantify and monitor coating and metal degradation from its earliest stages under both laboratory and field conditions.

DETAILED DESCRIPTION OF THE PREFERRED EMBODIMENTS

The invention provides a portable, hand-held, in-situ electrochemical sensor capable of detecting and monitoring corrosion of an actual structure from the earliest stages of deterioration. The sensor utilizes electrochemical impedance spectroscopy (EIS) for investigating corrosion and coating degradation.

Figure 1:
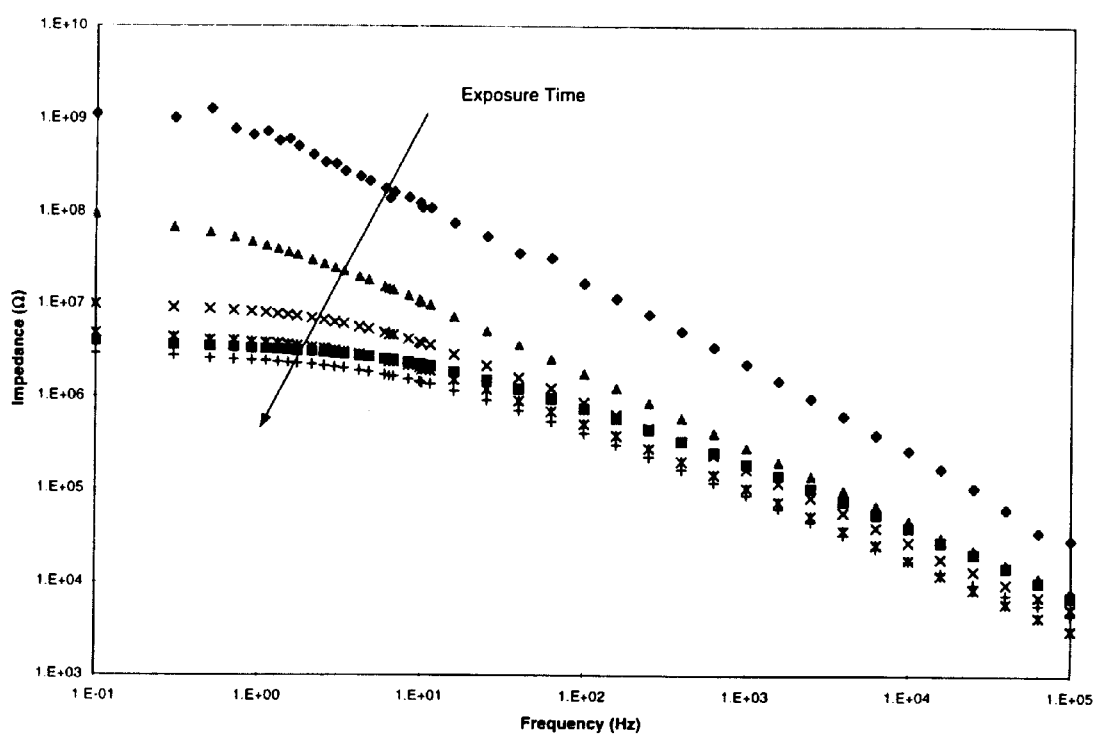
FIG. 1 is an impedance spectrum for painted aluminum following immersion for different periods of salt water exposure.

Referring to the drawings, FIG. 1 is a plot of an impedance spectrum for painted aluminum following immersion for different periods of salt water exposure. The figure shows that initially the coated metal demonstrates capacitive behavior with very high impedance at low frequencies. As the coating degrades during immersion, its resistance decreases and the impedance become independent of frequency at low frequencies.

Figure 2:
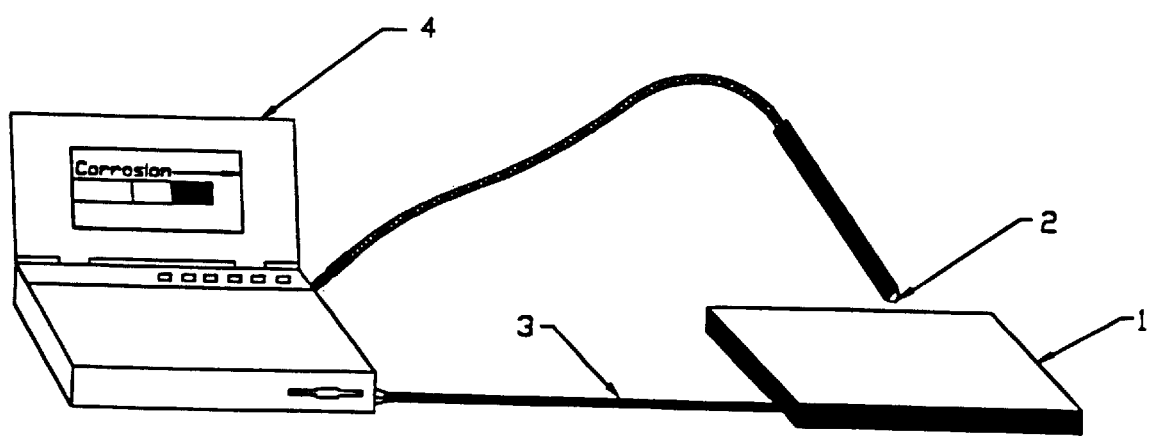
FIG. 2 is a diagrammatic representation of the pen-like sensing device with attached metal tip 2, that serves as the counter and reference electrode. The cable which is attached to 2, is connected to the potentiostat 4. The working electrode 1, is the coated metal being tested and connected to the potentiostat with an attached wire 3.

FIG. 2 is a drawing of a portable hand-held in-situ sensor with a metal tip 2, which acts as a reference and counter electrode. 2 is encased in a nonconductive plastic shield in the form of a pen-like holder for easy grasping in order to hold the tip of the electrode 2 onto the working painted metal 1 that is being tested. A cable is attached to the top of the pen-like electrode 2, to facilitate an easy electrical connection to a potentiostat 4. The working electrode 1, has a cable attached 3, for electrical connection to the potentiostat 4.

Figure 3:
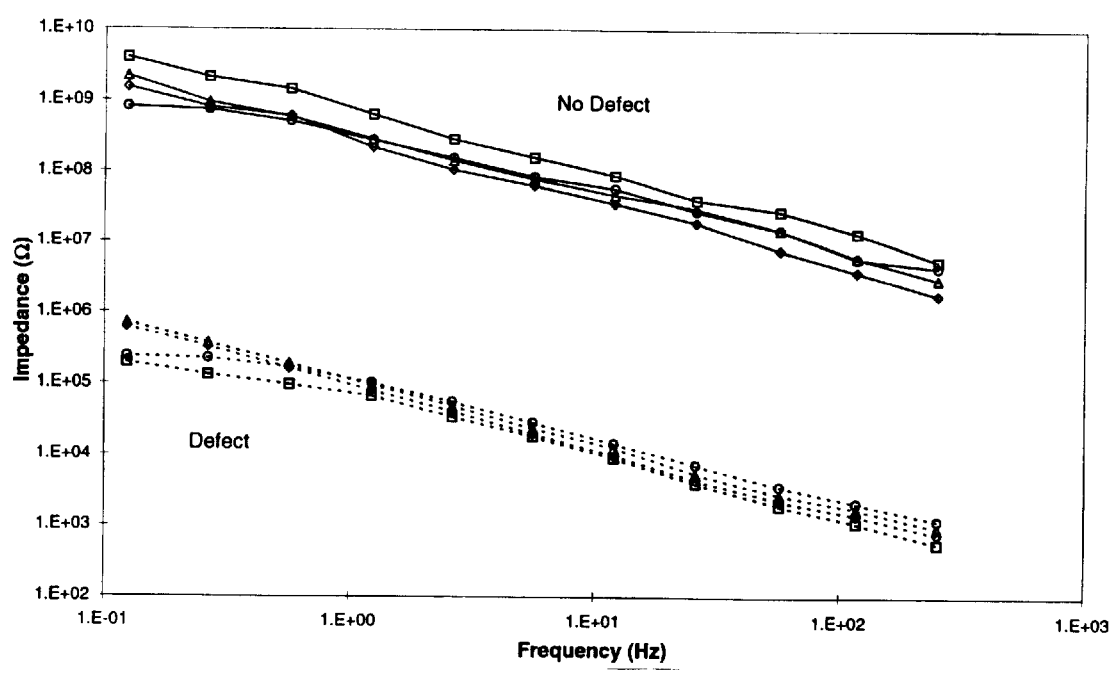
FIG. 3 is a graphic representation of impedance spectra of epoxy-polyimide painted aluminum with and without a scratched defect using both a conventional three-electrode measurement and measurements made using three different embodiments of the present invention.

FIG. 3 is a series of impedance spectra of epoxy-polyamide painted aluminum with and without a scratch defect. Each of the three variation of the hand-held probe gives results very similar to the conventional three-electrode measurements. Each measurement very clearly reflects the presence of a gross defect such as a scratch.

Figure 4:
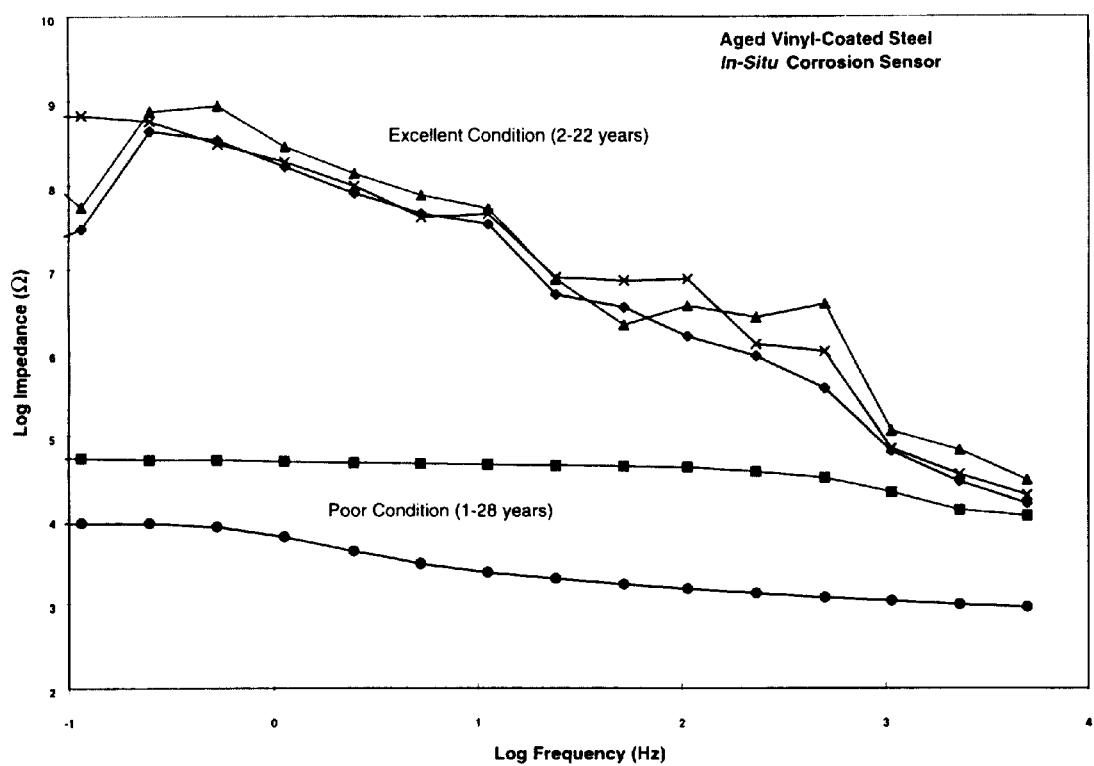
FIG. 4 is a graphic representation of vinyl-coated steel panels exposed to ambient fresh water obtained using the present invention.

FIG. 4 is a series of impedance spectra of vinyl-coated steel panels exposed to ambient fresh water for excellent condition even after 22 years of exposure; others were severely deteriorated even after one year. The correlation using the portable, hand-held in-situ electrochemical sensor is excellent. The coatings that appeared in excellent condition exhibited very high impedance with predominately capacitive behavior. In contrast, those coatings that were in poor condition with numerous blisters or rusty areas had very low impedance and mostly resistive behavior.

Figure 5:
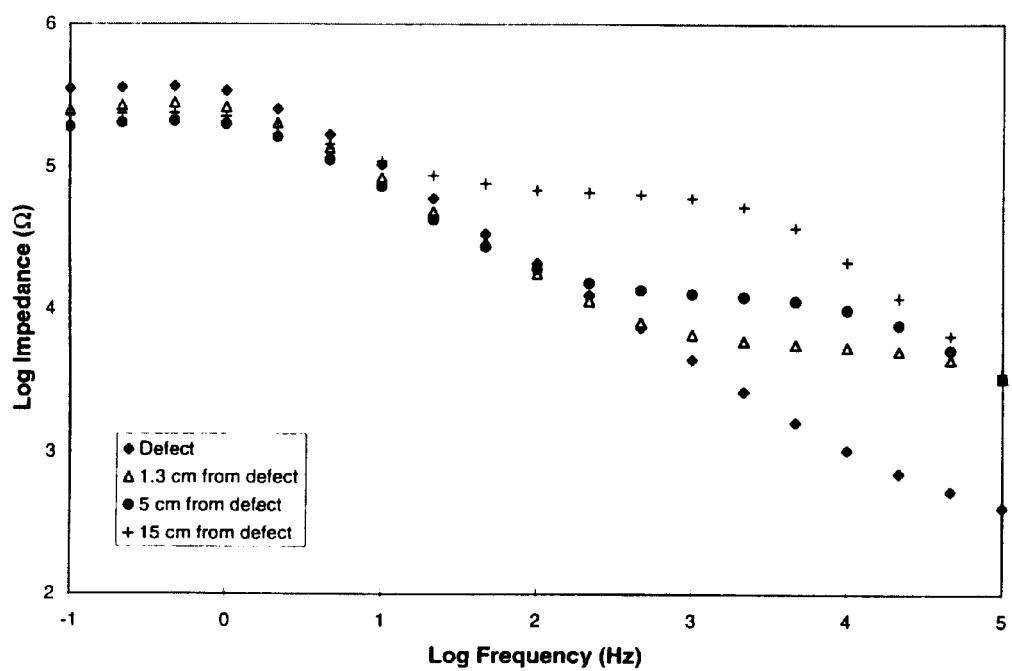
FIG. 5 is impedance spectra for a painted aluminum specimen with a scratch to simulate a coating defect.

FIG. 5 is a series of impedance spectra for a painted aluminum specimen with a scratch to simulate a coating defect. As the portable, hand-held, in-situ sensor was moved further from the defect, a plateau region at intermediate frequencies appears and corresponds to a conduction path along the surface.

We claim:

1. A method for early detection of electrochemical corrosion of a coated or an uncoated surface of a metal structure utilizing electrochemical impedance spectroscopy, comprising the steps of:

(a) providing an electrochemical impedance spectrometer, said spectrometer comprising a computer controlled potentiostat and a sensor device which comprises a metal tip, said sensor device functions as both a counter and reference electrode;

(b) placing the metal tip of the sensor device directly onto the top surface of the coated or uncoated surface of the metal structure;

(c) wetting the surface of the metal structure around the metal tip with an electrolyte, the metal tip and the area covered by the electrolyte thereby defining a controlled detection area;

(d) applying an AC voltage from the potentiostat across the metal tip and the metal structure to be tested, the metal structure thereby functioning as a working electrode;

(e) measuring the resulting AC current thus obtaining a first reading;

(f) performing steps (d) and (e) at different frequencies of AC voltage to obtain multiple readings;

(g) calculating an impedance magnitude and phase for each obtained reading, thereby generating an impedance spectrum over the entire applied frequency range;

(h) comparing the generated impedance spectrum of the controlled detection area with the impedance spectrum of previously determined measurements of metallic structures in different stages of known surface corrosion to determine the stage of surface corrosion of the metal structure being tested.

* * * * *